United States Patent [19]

Paciorek et al.

[11] Patent Number: 5,026,893

[45] Date of Patent: Jun. 25, 1991

[54] POLYSILAHYDROCARBON LUBRICANTS

[75] Inventors: Kazimiera J. L. Paciorek, Corona del Mar; Joseph G. Shih, La Palma; Bruce B. Randolph, Newport Beach, all of Calif.; Carl E. Snyder, Jr., Trotwood, Ohio

[73] Assignee: Lubricating Specialties Company, Pico Rivera, Calif.

[21] Appl. No.: 535,606

[22] Filed: Jun. 11, 1990

[51] Int. Cl.$^5$ ............................................. C07F 7/08
[52] U.S. Cl. ................................................... 556/435
[58] Field of Search ........................................ 556/435

[56] References Cited

U.S. PATENT DOCUMENTS 2,740,802  4/1956  Wagner et al. ................... 556/435
4,788,312  11/1988  Paciorek et al. ................. 556/435

Primary Examiner—Paul F. Shaver
Attorney, Agent, or Firm—Grant L. Hubbard

[57] ABSTRACT

Polysilahydrocarbons, such as tetrasilanes, are prepared by reaction of alkenyl organometallic compounds with alkyltrihalosilanes, followed by further reaction of the alkyltrialkenylsilane intermediates with trihalosilane and the subsequent substitution of the halogen atoms in the second intermediate by alkyl groups.

17 Claims, No Drawings

POLYSILAHYDROCARBON LUBRICANTS

RIGHTS OF THE GOVERNMENT

This invention was made with government support under Contract No. F33615-87-C-5328, awarded by the Department of the Air Force. The government has certain rights in the invention.

FIELD OF INVENTION

The present invention relates to a novel family of polysilahydrocarbon synthetic lubricant base stocks. More particularly, it relates to the preparation of tetrasilahydrocarbons and pentasilahydrocarbons and the reactive intermediates giving these compositions.

BACKGROUND OF THE INVENTION

A wide range of synthetic base stocks have been developed to alleviate the deficiencies of petroleum base stocks, for example, polyalphaolefins, esters, silicones, perfluorinated polyethers, and the like. For specific applications, in particular for liquid space lubricants, materials are required which exhibit extremely low volatility and specific viscosity-temperature properties enabling them to perform under extreme conditions. The perfluoroalkylethers, a product of Montedison described in U.S. Pat. No. 3,715,378, although meeting the above criteria, present corrosion problems due to the presence of fluorine. The monosilahydrocarbons described, for example, by C. E. Snyder et al., *ASLE Transactions*, Vol. 25, No. 3, pp. 298–308 (1982), have been shown to be superior to synthetic hydrocarbons, such as the polyalphaolefins, in viscosity-temperature properties, oxidative stability, and especially thermal stability, while additionally having advantages over silicones (polysiloxanes) in lubricity and bulk modulus. It is evident that incorporation of the silicon atom into the hydrocarbon skeleton can improve the utility of the structure for synthetic lubricant purposes.

However, the desirable effects of the silicon atom in the monosilahydrocarbons of the prior art become attenuated as the alkyl chains therein are increased beyond a certain length. Monosilahydrocarbons containing, for example, 90 or more carbon atoms would almost certainly be solids, not fluids, at room temperature. The molecular weight increase is mandatory to attain the required low volatility and sufficiently high viscosity to permit operation at elevated temperatures.

The trisilahydrocarbons described by U.S. Pat. No. 4,788,312 alleviated, to a high degree, the limitations inherent in monosilahydrocarbons and provided base fluids for certain applications. However, for very specific uses, where low volatility and particular viscosity characteristics are required, these materials are inadequate. A new class of silahydrocarbons is thus necessary which will exhibit the viscosity-volatility-temperature properties not achievable by the type of compositions currently known. It is further desirable for this new class of silahydrocarbons to be prepared from readily accessible raw materials. It is additionally desirable to have available relatively simple silicon-containing chemical intermediates, which, by the proper choice of reagents and conditions, could be converted into numerous silahydrocarbon structures designed to have properties suitable for specific applications. Our invention satisfies all these objectives.

We are not aware of the use of tetrasilahydrocarbons or pentasilahydrocarbons of our invention in synthetic lubricant applications. These tetrasilahydrocarbons and the chemical intermediates employed in their preparation and disclosed herein are, to the best of our knowledge, new chemical compounds previously unknown.

DETAILED DESCRIPTION OF THE INVENTION

We have discovered a novel class of synthetic lubricant base stock consisting of tetrasilahydrocarbons having the general structure

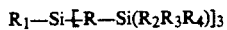

wherein $R_1$, $R_2$, $R_3$, and $R_4$ represent alkyl groups having from one to 20 carbon atoms, and —R— represents an alkylene group having from three to 10 carbon atoms. It is preferable that the alkyl and alkylene groups be unbranched; that is, —R— is preferably $+CH_2 +_n$, wherein n is from three to 10, and $R_1$, $R_2$, $R_3$ and $R_4$ are methyl, ethyl, n-propyl, n-butyl, and so on, up to n-eicosyl. However, a certain amount of branching within the alkyl and alkylene moieties may be tolerable if it does not adversely affect desired lubricant characteristics. Likewise, the presence of aryl substituents (phenyl and the like) would generally be less desirable in the tetrasilahydrocarbons of our invention but might be tolerated if the product properties are not seriously compromised. $R_1$, $R_2$, $R_3$, and $R_4$ may be the same or different alkyl groups, and —R— is considered to include mixtures of alkylene groups having different chain lengths within the three- to 10-carbon range. As will be shown below, one of the outstanding characteristics of the tetrasilahydrocarbons of our invention is the ease with which, by suitable choice of chemical raw materials, a wide variety of different compositions can be prepared.

The tetrasilahydrocarbon lubricant base stocks of our invention are prepared by reaction of novel intermediates represented by $R_1Si[+CH_2+_nSiX_3]_3$ formed from alkyltrichlorosilane, organometallic reagents, and trichlorosilane:

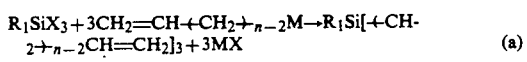

(a)

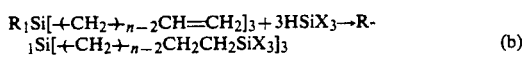

(b)

followed by reaction with an organometallic compound:

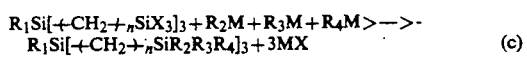

(c)

The detailed description of each of the steps delineated above is given below. The sequence of Steps (a), (b), and (c) permits the preparation of pentasilahydrocarbons of the general formula $Si[+CH_2+_{n-2}CH_2CH_2SiR_2R_3R_4]_4$ obtained by using in Step (a) the tetrahalosilane instead of the alkyltrihalosilane.

(a) Reaction of an alkyltrihalosilane, $R_1SiX_3$, wherein $R_1$ is an alkyl group having from one to 20 carbon atoms and X is a halogen, preferably chlorine or bromine, or tetrahalosilane, $SiX_4$, with an alkenyl organometallic reagent, $CH_2=CH+CH_2+_{n-2}M$. Any appropriate organometallic reagent can be used, including organomagnesium and organolithium reagents, with the alkenyl group having from three to 10 carbon atoms, thereby forming the intermediate alkyltrialkenylsilane of the general formula, $R_1Si$-

$[+CH_2+_{n-2}CH=CH_2]_3$, or tetraalkenylsilane, of the general formula $Si[+CH_2+_{n-2}CH=CH_2]_4$. A considerable excess of organometallic reagent is employed in order to ensure that all the halogens on the alkyltrihalosilane or the tetrahalosilane are replaced by the alkenyl group of the organometallic reagent. A suitable solvent is used, such as tetrahydrofuran or other ethers. The reaction is conducted under an inert atmosphere as represented by nitrogen or argon.

(b) Condensation of the alkyltrialkenylsilane or the tetraalkenylsilane from Step (a) with a trihalosilane to form the alkyl-tris(trihalosilylalkyl)silane of the general formula $R_1Si[+CH_2+_{n-2}CH_2CH_2SiX_3]_3$ and the tetra(trihalosilylalkyl)silane of the general formula $Si[+CH_2)_{n-2}CH_2CH_2SiX_3]_4$, wherein X is a halogen, preferably chlorine or bromine. Addition of the trihalosilane to the olefinic compounds is carried out in the presence of a suitable platinum, palladium, or rhodium catalyst. A number of platinum-containing catalysts can be used, including hexachloroplatinic acid, platinum acetylacetonate and other catalysts apparent to those skilled in the art. The compounds prepared in Step (b) are believed to be new, heretofore unknown, compositions. Moreover, these compounds are of an exceptional degree of utility, in view of the vast numbers of synthetic lubricant products that can be prepared therefrom.

(c) Replacement of the halogen atoms in the intermediates of Step (b) with alkyl groups is performed by treatment with organometallic compounds of suitable reactivity. The alkyl groups can contain from one to 20 carbon atoms. Suitable organometallic compounds include the alkyl lithium compounds, alkyl magnesium halides (Grignard reagents), dialkyl magnesium compounds, alkyl sodium compounds, dialkyl zinc compounds, and the like, with the alkyl lithium compounds and the Grignard reagents being the preferred reagents. A single organometallic compound, such as $H(CH_2)_mLi$, or a mixture of organometallic compounds, such as $H(CH_2)_mLi$, $H(CH_2)_nLi$, and $H(CH_2)_rLi$, where m, n, and r are different and can vary from one to 20, can be employed to achieve either the uniform or the mixed alkyl substitution in the final tetrasilahydrocarbon or pentasilahydrocarbon products. A suitable organometallic reaction solvent, such as diethyl ether, tetrahydrofuran, and others apparent to those skilled in the art, can be used. As an alternative to the use of organometallic compounds, the halogen atoms can be replaced by hydrogen by treatment with metallohydride reducing agents, such as lithium aluminum hydride, sodium hydride, sodium borohydride, and others apparent to those skilled in the art. The resulting —Si—H compounds can then be added to olefins in the presence of a suitable catalyst, such as hexachloroplatinic acid, platinum acetylacetonate, and other catalysts apparent to those skilled in the art, to form the final alkylsilicon products. The use of the organometallic compounds is preferable in order to avoid the two-step reaction sequence required by the alternate route. In either case, Step (c) will result in the formation of a tetrasilahydrocarbon or pentasilahydrocarbon of our invention having the general formulae $R_1—Si[—R—Si(R_2R_3R_4)]_3$ and $Si[—R—Si(R_2R_3R_4)]_4$, respectively.

As would be obvious to the skilled worker, numerous modifications in the structure of the final tetrasilahydrocarbon and pentasilahydrocarbon products can be achieved by the appropriate choice of the reactants used in each of the different steps. Higher molecular weight tetrasilahydrocarbons may be prepared (1) by the use of a longer chain alkyltrihalosilane in Step (a), (2) by the use of longer chain alkenyl groups in the alkenyl organometallic reagent in Step (a), and (3) by the use of longer alkyl chain lithium compounds or alkylmagnesium halides and the like in Step (c). The aspects listed in (2) and (3) apply also to pentasilahydrocarbons. Conversely, the use of shorter chain alkyl and shorter chain alkenyl compounds will produce final tetrasilahydrocarbons and pentasilahydrocarbons of relatively low molecular weight to provide lower viscosity materials. All the different modifications to tailor the properties of the polysilahydrocarbons should be obvious to those skilled in the art. Reactants needed for the syntheses are, in general, readily available. Thus, the polysilahydrocarbons of our invention, as a class of synthetic lubricant, provide the versatility allowing the tailoring of compositions to achieve a wide range of lubricant properties.

The preparation of polysilahydrocarbons of our invention will now be illustrated by specific examples; however, these are not to be construed as unduly limiting the scope of the subject invention.

EXAMPLE 1

Preparation of
n-Octyl-tris-[3-(trimethylsilyl)propyl]silane

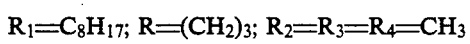

Step (a)

Into a 2 L three-neck round bottom flask equipped with two stoppers, reflux condenser, nitrogen bypass inlet, and magnetic stirring bar were added freshly distilled tetrahydrofuran (600 Ml) and allylmagnesium chloride (800 Ml, 2.0M in THF, 1.6 mol). In an inert atmosphere enclosure, n-octyltrichlorosilane (100.00 g, 0.404 mol) was placed in an addition funnel. Subsequently, the addition funnel was attached to the flask containing allylmagnesium chloride. n-Octyltrichlorosilane was then slowly added to the reaction mixture (cooled to 0° C.). A white precipitate started to appear immediately. After the completion of addition, the reaction mixture was heated gradually to reflux; refluxing was continued for 96 hours. It was then cooled in an ice-water bath, and hydrochloric acid (425 Ml, 1.2N) was added cautiously with vigorous stirring. The organic layer was separated, and the aqueous layer was extracted with diethyl ether (2×150 Ml). The ethereal extracts and the original organic layer were combined, washed once with saturated aqueous sodium bicarbonate solution, and dried over magnesium sulfate. Removal of the solvent and vacuum fractionation yielded 98.8 g (92.4% yield) b.p. 101°–105° C. at 0.001 mm Hg, of n-octyltriallylsilane.

Step (b)

In an inert atmosphere enclosure, into a 200 Ml glass ampoule equipped with a Teflon/glass valve and magnetic stirring bar were added platinum acetylacetonate (0.04 g, 0.1 mmol) and n-octyltriallylsilane (20.0 g, 75.6 mmol). Subsequently, trichlorosilane (87.17 g, 643.5 mmol) was distilled into the ampoule using a vacuum line transfer system. The ampoule was placed in an oil bath and heated slowly to 40° C., at which temperature it was kept for 12 days. The excess trichlorosilane was removed in vacuo, and distillation of the product yielded 37.6 g (74.1% yield), b.p. 202°–20° C. at 0.001 mm Hg of n-octyl-tris-[3-(trichlorosilyl)propyl]silane.

Step (c)

Into a 500 Ml three-neck round bottom flask equipped with rubber septum, reflux condenser, nitrogen bypass inlet, and magnetic stirring bar was introduced, via a flex-needle, methyllithium (100 Ml, 1.4M in diethyl ether, 140 mmol and 100 Ml, 1.5M methyllithium-lithium bromide complex in diethyl ether, 150 mmol) under a strong flow of nitrogen. In an inert atmosphere enclosure, to a 50 Ml addition funnel was added n-octyl-tris-[3-(trichlorosilyl)propyl]silane (17.0 g, 25.3 mmol). The addition funnel was attached to the flask containing methyllithium, and n-octyl-tris-[3-(trichlorosilyl)propyl]silane was subsequently added to the ethereal solution of methyllithium (cooled to 0° C.) over a period of 30 minutes. A white powdery precipitate appeared immediately. The reaction was exothermic. After the addition was completed, the reaction mixture was heated at reflux temperature for 20 hours. Subsequently, it was cooled in an ice-water bath, and hydrochloric acid (250 Ml 1.2N) was cautiously added. The reaction mixture separated into two layers on standing. The organic layer was collected, and the aqueous layer was extracted with diethyl ether (150 Ml). The organic layers were combined and dried over magnesium sulfate. Solvent was removed under reduced pressure, and fractionation in vacuo yielded 9.71 g (78.3%), b.p. 143°–147° C. at 0.001 mm Hg, of n-octyl-tris-[3-(trimethylsilyl)propyl]silane. The tetrasilahydrocarbon had a kinematic viscosity of 2.82 centistokes at 100° C., a kinematic viscosity of 10.5 centistokes at 40° C., and a viscosity index of 115. Onset of volatilization under 0.44 mm Hg pressure, based on thermogravimetric analysis, was at 85° C.

EXAMPLE 2

Preparation of n-octyl-tris-[3-(trioctylsilyl)propyl]silane

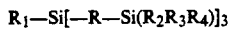

$R_1=R_2=R_3=R_4=C_8H_{17}$; $R=(CH_2)_3$

Step (c)

Under strong nitrogen flow, into a 1 L three-neck round bottom flask equipped with rubber septum, reflux condenser, nitrogen bypass inlet, and magnetic stirring bar were added, via a flex-needle, n-octylmagnesium chloride (310 Ml, 2.0M in tetrahydrofuran, 620 mmol) and tetrahydrofuran (350 Ml). In an inert atmosphere enclosure, to a 50 Ml addition funnel was added n-octyl-tris-[3-(trichlorosilyl)propyl]silane (23.0 g, 34.3 mmol, prepared as in Example 1, Step (b)). The addition funnel was attached to the flask containing n-octylmagnesium chloride, and n-octyl-tris-[3-(trichlorosilyl)propyl]silane was subsequently added to the tetrahydrofuran solution of n-octylmagnesium chloride over a period of 25 minutes. The reaction was exothermic. After completion of addition, the reaction mixture was heated at reflux temperature for 10 days and then allowed to cool to room temperature. At this time it was cooled in an ice-water bath and hydrochloric acid (500 Ml, 1.2N) was cautiously added. The reaction mixture separated into two layers on standing. The aqueous layer was washed with diethyl ether (2×200 Ml). The organic layers were combined, washed with water (200 Ml), and dried over magnesium sulfate, and the solvent removed under reduced pressure. Purification by silica gel column chromatography yielded 36.7 g (78.1%) of n-octyl-tris-[3-(trioctylsilyl)propyl]silane. This tetrasilahydrocarbon had a kinematic viscosity of 66.2 centistokes at 40° C., a kinematic viscosity of 12.5 centistokes at 100° C., and a viscosity index of 191. Onset of volatilization under 0.44 mm Hg pressure, based on the thermogravimetric analysis, was at 275° C. Thus, it is shown that by the use of a higher alkyl organometallic compound in Step (c), a far more viscous tetrasilahydrocarbon product with lower volatility can be prepared from the same intermediate as was used to prepare the relatively low viscosity base stock of Example 1.

EXAMPLE 3

Preparation of n-octyl-tris-[3-(tridecylsilyl)propyl]silane

$R_1=n-C_8H_{17}$; $R=(CH_2)_3$; $R_2=R_3=R_4=n-C_{10}H_{21}$

Step (c)

Under a strong nitrogen flow, into a 2 L three-neck round bottom flask equipped with rubber septum, reflux condenser, nitrogen bypass inlet, and magnetic stirring bar was introduced, via a flex-needle, a tetrahydrofuran solution of n-decylmagnesium bromide (114.7 g, 467 mmol). In an inert atmosphere enclosure, into a 50 Ml addition funnel was added n-octyl-tris-[3-(trichlorosilyl)propyl]silane (27.85 g, 41.5 mmol, prepared by the procedure described in Example 1, Step (b)). The addition funnel was attached to the flask containing the n-decylmagnesium bromide solution, and n-octyl-tris-[3-(trichlorosilyl)propyl]silane was added over a period of 40 minutes. The reaction mixture was kept at 50° C. for 15 hours, then allowed to cool to room temperature, and an additional solution of n-decylmagnesium bromide (114.6 g, 467 mmol) in tetrahydrofuran was added into the reaction flask. The reaction mixture was then heated at reflux temperature for 164 hours. After cooling in an ice-water bath, hydrochloric acid (500 Ml, 1.2N) was cautiously added. The reaction mixture separated into two layers on standing. These were separated, and the aqueous layer was extracted with diethyl ether (2×200 Ml). The organic layers were combined, washed with water (200 Ml), and dried over magnesium sulfate, and the solvent removed under reduced pressure. Purification by silica gel column chromatography yielded 54.5 g (81.0%) of n-octyl-tris-[3-(tridecylsilyl)-propyl]silane. This tetrasilahydrocarbon had a kinematic viscosity of 89.7 centistokes at 40° C., a kinematic viscosity of 15.4 centistokes at 100° C., and a viscosity index of 182. Onset of volatilization under 0.44 mm Hg pressure, based on thermogravimetric analysis, was at 285° C.

EXAMPLE 4

Preparation of n-octyl-tris-[3-(tridodecylsilyl)propyl]silane

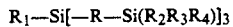

$R_1=n-C_8H_{17}$; $R=(CH_2)_3$; $R_2=R_3=R_4=n-C_{12}H_{25}$

Step (c)

Under a strong nitrogen flow, into a 2 L three-neck round bottom flask equipped with rubber septum, reflux condenser, nitrogen bypass inlet, and magnetic stirring bar were introduced freshly distilled tetrahydrofuran (350 Ml) and n-dodecylmagnesium bromide (800 Ml, 1.0M in diethyl ether, 800 mmol). In an inert atmosphere enclosure, into a 500 Ml addition funnel was added n-octyl-tris-[3-(trichlorosilyl)propyl]silane (30.0 g, 44.7 mmol, prepared by the procedure described in Example 1, Step (b)). The addition funnel was attached to the flask containing n-dodecylmagnesium bromide, and n-octyl-tris-[3-(trichlorosilyl)propyl]silane was added to the n-dodecylmagnesium bromide solution over a period of 45 minutes. The reaction was only slightly exothermic. The reaction mixture was heated at reflux temperature for 186 hours, then cooled to room temperature, and an ether solution of methyllithium (50 Ml, 1.5M) was added. The reaction mixture was heated at reflux temperature again for an additional 24 hours. After it was cooled in an ice-water bath, hydrochloric acid (500 Ml, 1.2N) was cautiously added. The reaction mixture separated into two layers on standing. The aqueous layer was extracted with diethyl ether (2×200 Ml). The organic layers were combined, washed once with water (200 Ml), and dried over magnesium sulfate, and the solvent removed under reduced pressure. Purification by silica gel column chromatography yielded 36.8 g (43.6%) of n-octyl-tris-[3-(tridodecylsilyl)propyl]silane. This tetrasilahydrocarbon had a kinematic viscosity of 105 centistokes at 40° C., a kinematic viscosity of 17.5 centistokes at 100° C., and a viscosity index of 183. Onset of volatilization under 0.43 mm Hg pressure, based on the thermogravimetric analysis, was at 285° C.

The foregoing examples illustrate the wide range of properties achievable with this type of compositions. As would be obvious to one skilled in the art, numerous modifications can be made herein, without departing from the scope of our invention. The tetrasilahydrocarbon and pentasilahydrocarbon synthetic lubricant base stocks can be used as prepared; or alternately, they can be formulated with additives designed to impart additional desirable properties appropriate to the application, for example, antioxidants, corrosion inhibitors, antiwear agents, detergents, antifoam agents, and the like. The above examples are for the purpose of illustration only and are not meant to be limiting within the scope of the following claims.

INDUSTRIAL APPLICATION

This invention has application in the chemical process industries and in the manufacture of lubricants.

What is claimed is:

1. A tetrasilahydrocarbon synthetic lubricant base stock having the general formula

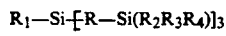

$$R_1-Si-[R-Si(R_2R_3R_4)]_3$$

wherein $R_1$, $R_2$, $R_3$, and $R_4$ are alkyl groups having from one to 20 carbon atoms and mixtures thereof, and —R— is an alkylene group, or mixture of alkylene groups, having from three to 10 carbon atoms.

2. The tetrasilahydrocarbon synthetic lubricant base stock of claim 1, wherein the alkyl and alkylene groups are unbranched.

3. The tetrasilahydrocarbon synthetic lubricant base stock of claim 1, wherein $R_1$ is n-octyl, $R_2$, $R_3$, and $R_4$ are all methyl, and the alkylene group is trimethylene.

4. The tetrasilahydrocarbon synthetic lubricant base stock of claim 1, wherein $R_1$, $R_2$, $R_3$, and $R_4$ are all n-octyl, and the alkylene group is trimethylene.

5. The tetrasilahydrocarbon synthetic lubricant base stock of claim 1, wherein $R_1$ is n-octyl, $R_2$, $R_3$, and $R_4$ are all n-decyl, and the alkylene group is trimethylene.

6. The tetrasilahydrocarbon synthetic lubricant base stock of claim 1, wherein $R_1$ is n-octyl, $R_2$, $R_3$, and $R_4$ are all n-dodecyl, and the alkylene group is trimethylene.

7. A pentasilahydrocarbon synthetic lubricant base stock having the general formula

$$Si-R-[Si(R_2R_3R_4)]_4$$

wherein $R_2$, $R_3$, and $R_4$ are alkyl groups having from one to 20 carbon atoms, and mixtures thereof, and —R— is an alkylene group, or mixture of alkylene groups, having from three to 10 carbon atoms.

8. A tetrasilahydrocarbon synthetic lubricant base stock prepared by the following steps:
   (a) reaction of an alkenyl organometallic reagent, the alkenyl group having from three to 10 carbon atoms, or mixtures of said alkenyl organometallic reagents with an alkyltrihalosilane, the alkyl group having from one to 20 carbon atoms, to form an intermediate alkyltrialkenylsilane;
   (b) condensation of the alkyltrialkenylsilane from Step (a) with a trihalosilane, wherein the halogen is either chlorine or bromine, in the presence of a catalyst to form alkyl-tris-[ω-(trihalosilyl)alkyl]silane; and
   (c) replacement of the halogen atoms in the product of Step (b) by alkyl groups, having from one to 20 carbon atoms, by treatment with an organometallic compound, or a mixture of organometallic compounds, to form the final alkyl-tris-[ω-(trialkylsilyl)alkyl]silane products.

9. A tetrasilahydrocarbon synthetic lubricant base stock according to claim 8 wherein said organometallic reagent comprises alkenylmagnesium halide Grignard reagents, dialkenylmagnesium compounds, and alkenyllithium compounds.

10. A tetrasilahydrocarbon synthetic lubricant base stock according to claim 9, wherein said process is carried out in a Grignard or organolithium reagent stable solvent.

11. A tetrasilahydrocarbon synthetic lubricant base stock according to claim 8 wherein said catalyst comprises hexachloroplatinic acid or platinum acetylacetonate.

12. A tetrasilahydrocarbon synthetic lubricant base stock according to claim 8 wherein said organometallic compound comprises alkyllithium compounds, alkylmagnesium halide Grignard reagents, dialkylmagnesium compounds, alkylsodium compounds, dialkylzinc compounds, and mixtures of said organometallic compounds.

13. A method of preparing tetrasilahydrocarbon synthetic lubricant base stock comprising the following steps:
   (a) reacting an alkenyl organometallic reagent, the alkenyl group having from three to 10 carbon atoms, or mixtures of said alkenyl organometallic reagents with an alkyltrihalosilane, the alkyl group having from one to 20 carbon atoms, to form an intermediate alkyltrialkenylsilane;

(b) condensing the alkyltrialkenylsilane from Step (a) with a trihalosilane, wherein the halogen is either chlorine or bromine, in the presence of a catalyst to form alkyl-tris-[ω-(trihalosilyl)alkyl]silane; and (c) replacing the halogen atoms in the product of Step (b) by alkyl groups, having from one to 20 carbon atoms, by treatment with an organometallic compound, or a mixture of organometallic compounds, to form the final alkyl-tris-[ω-(trialkylsilyl)alkyl]silane products.

14. The process of claim 13 wherein said organometallic reagent comprises alkenylmagnesium halide Grignard reagents, dialkenylmagnesium compounds, and alkenyllithium compounds.

15. The process of claim 14, wherein said process is carried out in a Grignard or organolithium reagent stable solvent.

16. The process of claim 13 wherein said catalyst comprises hexachloroplatinic acid or platinum acetylacetonate.

17. The process of claim 13 wherein said organometallic compound comprises alkyllithium compounds, alkylmagnesium halide Grignard reagents, dialkylmagnesium compounds, alkylsodium compounds, dialkylzinc compounds, and mixtures of said organometallic compounds.

* * * * *